US006245895B1

(12) United States Patent
Sällberg

(10) Patent No.: US 6,245,895 B1
(45) Date of Patent: *Jun. 12, 2001

(54) ANTIGEN/ANTIBODY SPECIFICITY EXCHANGER

(75) Inventor: Matti Sällberg, Stockholm (SE)

(73) Assignee: Tripep AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,106

(22) Filed: Mar. 21, 2000

Related U.S. Application Data

(63) Continuation of application No. 09/246,258, filed on Feb. 8, 1999, now Pat. No. 6,040,137, which is a continuation of application No. 08/737,085, filed on Dec. 27, 1996, now Pat. No. 5,869,232.

(30) Foreign Application Priority Data

Apr. 28, 1994 (SE) .................................................. 9401460

(51) Int. Cl.[7] ...................................................... C07K 1/00
(52) U.S. Cl. ................................................ 530/350; 435/5
(58) Field of Search ................................ 435/5, 7.1, 7.9, 435/7.92; 530/324–330, 350; 424/184.1, 185.1, 188.1, 189.1, 190.1, 192.1; 514/2

(56) References Cited

U.S. PATENT DOCUMENTS

| | | | |
|---|---|---|---|
| 5,091,513 | 2/1992 | Huston et al. | 530/387 |
| 5,196,510 | 3/1993 | Rodwell et al. | 530/324 |
| 5,260,189 | 11/1993 | Formoso et al. | 435/5 |

FOREIGN PATENT DOCUMENTS

| | | |
|---|---|---|
| 0 182 546 A2 | 5/1986 | (EP) . |
| WO 93/15210 | 8/1993 | (WO) . |
| WO 94/13804 | 6/1994 | (WO) . |
| WO 95/08577 | 3/1995 | (WO) . |

OTHER PUBLICATIONS

Bianchi, et al., *Int J Pept Protein Res*, 41(4):385–393, Apr. 1993, "Chemical Synthesis of a Designed Beta–Protein Through the Flow–Polyamide Method."

Bianchi, et al., *Int J Pept Protein Res*, 42(1): 93–96, Jul. 1993, "Affinity Purification of a Difficult–Sequence Protein: Implications for the Inclusion of Capping in Synthetic Protocols."

Holliger, et al., *Proc Natl Acad Sci USA*, 90: 6444–6448, Jul. 1993, "'Diabodies': Small Bivalent and Bispecific Antibody Fragments."

Levi, et al., *Proc Natl Acad Sci USA*, 90: 4374–4378, May 1993, "A Complementarity–Determining Region Synthetic Peptide Acts as a Miniantibody and Neutralizes Human Immunodificiency Virus Type 1 in vitro."

Saragovi, et al., *Science*, 253: 792–795, Aug. 16, 1991, "Design and Synthesis of a Mimetic from an Antibody Complementarity–Determining Region."

Tramontano, et al., *J. of Molecular Recognition*, 7(1): 9–24, 1994, "The Making of the Minibody: An Engineered Beta–Protein for the Display of Conformationally Constrained Peptides."

Zanetti, M., *Nature*, 355: 476–477 , Jan. 30, 1992, "Antigenized Antibodies."

*Primary Examiner*—Jeffrey Stucker
(74) *Attorney, Agent, or Firm*—Knobbe, Martens, Olson & Bear, LLP

(57) ABSTRACT

An antigen/antibody specificity exchanger is disclosed. It comprises: A) an amino-acid sequence corresponding to an amino-acid sequence of an antibody which specifically binds to a certain antigen, including hapten, B) linked by a link to C) an amino-acid sequence to which a certain antibody binds. Also, a diagnostic reagent comprising an antigen/antibody specificity exchanger according to the invention is disclosed. Said reagent may be e.g. used instead of antisera or monoclonal antibodies in in vitro testing systems, such as immunological tests. Further, a method of treating a disease or disorder caused by a known antigen in an individual in need of an increased number of antigen-specific antibodies is disclosed. In the method a tailor-made antigen/antibody specificity exchanger of the invention is issued. Said method may be e.g. used to redirect a patient's antibodies against poliovirus to fight HIV infection in said patient.

3 Claims, No Drawings

SEQUENCE LISTING

```
(1) GENERAL INFORMATION:

   (iii) NUMBER OF SEQUENCES: 23


(2) INFORMATION FOR SEQ ID NO: 1:

     (i) SEQUENCE CHARACTERISTICS:
          (A) LENGTH: 14 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 1:

Cys Asp Leu Ile Tyr Tyr Asp Tyr Glu Glu Asp Tyr Tyr Phe
 1               5                  10


(2) INFORMATION FOR SEQ ID NO: 2:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 2:

Cys Asp Leu Ile Tyr Tyr Asp Tyr Glu Glu Asp Tyr Tyr
 1               5                  10


(2) INFORMATION FOR SEQ ID NO: 3:

     (i) SEQUENCE CHARACTERISTICS:
          (A) LENGTH: 5 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 3:

Thr Tyr Ala Met Asn
 1               5


(2) INFORMATION FOR SEQ ID NO: 4:

     (i) SEQUENCE CHARACTERISTICS:
          (A) LENGTH: 19 amino acids
```

-continued (B) TYPE: amino acid
(C) STRANDEDNESS: single
(D) TOPOLOGY: linear (ii) MOLECULE TYPE: peptide (xi) SEQUENCE DESCRIPTION: SEQ ID NO: 4:

```
Arg Val Arg Ser Lys Ser Phe Asn Tyr Ala Thr Tyr Tyr Ala Asp Ser
 1               5                  10                  15

Val Lys Gly
```

(2) INFORMATION FOR SEQ ID NO: 5:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 5:

```
Pro Ala Gln Gly Ile Tyr Phe Asp Tyr Gly Gly Phe Ala Tyr
 1               5                  10
```

(2) INFORMATION FOR SEQ ID NO: 6:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 6:

```
Pro Pro Asn Ala Pro Ile Leu Ser
 1               5
```

(2) INFORMATION FOR SEQ ID NO: 7:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 7:

```
Arg Pro Pro Asn Ala Pro Ile Leu Ser Thr
 1               5                  10
```

(2) INFORMATION FOR SEQ ID NO: 8:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 8:

```
Lys Gly Ile Pro Ala Leu Thr Ala Val Gly Thr Gly
 1               5                  10
```

(2) INFORMATION FOR SEQ ID NO: 9:

-continued (i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 9:

```
Pro Ala His Ser Lys Gly Ile Pro Ala Leu Thr Ala
 1               5                   10
```

(2) INFORMATION FOR SEQ ID NO: 10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 10:

```
Trp Gly Cys Ser Gly Lys Leu Ile Cys Thr
 1               5                   10
```

(2) INFORMATION FOR SEQ ID NO: 11:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 11:

```
Cys Thr Thr Ala Val Pro Trp Asn Ala Ser
 1               5                   10
```

(2) INFORMATION FOR SEQ ID NO: 12:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 12:

```
Gln Arg Lys Thr Lys Arg Asn Thr Asn Arg Arg
 1               5                   10
```

(2) INFORMATION FOR SEQ ID NO: 13:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 13:

```
Cys Asp Leu Ile Tyr Tyr Asp Tyr Glu Glu Asp Tyr Tyr Phe Pro Pro
 1               5                   10                  15

Asn Ala Pro Ile Leu Ser
```

-continued

```
            20

(2) INFORMATION FOR SEQ ID NO: 14:

     (i) SEQUENCE CHARACTERISTICS:
          (A) LENGTH: 24 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 14:

Cys Asp Leu Ile Tyr Tyr Asp Tyr Glu Glu Asp Tyr Tyr Phe Arg Pro
 1               5                  10                  15

Pro Asn Ala Pro Ile Leu Ser Thr
            20

(2) INFORMATION FOR SEQ ID NO: 15:

     (i) SEQUENCE CHARACTERISTICS:
          (A) LENGTH: 26 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 15:

Cys Asp Leu Ile Tyr Tyr Asp Tyr Glu Glu Asp Tyr Tyr Phe Lys Glu
 1               5                  10                  15

Ile Pro Ala Leu Thr Ala Val Glu Thr Gly
            20                  25

(2) INFORMATION FOR SEQ ID NO: 16:

     (i) SEQUENCE CHARACTERISTICS:
          (A) LENGTH: 26 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 16:

Cys Asp Leu Ile Tyr Tyr Asp Tyr Glu Glu Asp Tyr Tyr Phe Pro Ala
 1               5                  10                  15

His Ser Lys Glu Ile Pro Ala Leu Thr Ala
            20                  25

(2) INFORMATION FOR SEQ ID NO: 17:

     (i) SEQUENCE CHARACTERISTICS:
          (A) LENGTH: 24 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO: 17:

Cys Asp Leu Ile Tyr Tyr Asp Tyr Glu Glu Asp Tyr Tyr Phe Trp Gly
 1               5                  10                  15

Cys Ser Gly Lys Leu Ile Cys Thr
            20
```

-continued (2) INFORMATION FOR SEQ ID NO: 18:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 18:

```
Cys Asp Leu Ile Tyr Tyr Asp Tyr Glu Glu Asp Tyr Tyr Phe Cys Thr
 1               5                  10                  15

Thr Ala Val Pro Trp Asn Ala Ser
            20
```

(2) INFORMATION FOR SEQ ID NO: 19:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 19:

```
Cys Asp Leu Ile Tyr Tyr Asp Tyr Glu Glu Asp Tyr Tyr Phe Lys Arg
 1               5                  10                  15

Pro Pro Asn Ala Pro Ile Leu Ser Thr
            20                  25
```

(2) INFORMATION FOR SEQ ID NO: 20:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 20:

```
Thr Tyr Ala Met Asn Pro Pro Asn Ala Pro Ile Leu Ser
 1               5                  10
```

(2) INFORMATION FOR SEQ ID NO: 21:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 21:

```
Arg Val Arg Ser Lys Ser Phe Asn Tyr Ala Thr Tyr Tyr Ala Asp Ser
 1               5                  10                  15

Val Lys Gly Pro Pro Asn Ala Pro Ile Leu Ser
            20                  25
```

(2) INFORMATION FOR SEQ ID NO: 22:

(i) SEQUENCE CHARACTERISTICS:
(A) LENGTH: 22 amino acids
(B) TYPE: amino acid
(C) STRANDEDNESS: single -continued

```
        (D) TOPOLOGY: linear

   (ii) MOLECULE TYPE: peptide

   (xi) SEQUENCE DESCRIPTION: SEQ ID NO: 22:

Pro Ala Gln Gly Ile Tyr Phe Asp Tyr Gly Gly Phe Ala Tyr Pro Pro
 1               5                  10                  15

Asn Ala Pro Ile Leu Ser
            20


(2) INFORMATION FOR SEQ ID NO: 23:

    (i) SEQUENCE CHARACTERISTICS:
        (A) LENGTH: 24 amino acids
        (B) TYPE: amino acid
        (C) STRANDEDNESS: single
        (D) TOPOLOGY: linear

   (ii) MOLECULE TYPE: peptide

   (xi) SEQUENCE DESCRIPTION: SEQ ID NO: 23:

Cys Asp Leu Ile Tyr Tyr Asp Tyr Glu Glu Asp Tyr Tyr Gln Arg Lys
 1               5                  10                  15

Thr Lys Arg Asn Thr Asn Arg Arg
            20
```

ANTIGEN/ANTIBODY SPECIFICITY EXCHANGER

This application is a continuation of prior application Ser. No. 09/246,258, filed Feb. 8, 1999, now U.S. Pat. No. 6,040,137 which is a continuation of prior application Ser. No. 08/737,085, filed Dec. 27, 1996, now U.S. Pat. No. 5,869,232.

The present invention relates to an antigen/antibody specificity exchanger, which comprises an amino-acid sequence which specifically binds to a certain antigen linked to an amino-acid sequence to which a certain antibody binds. In vitro the antigen/antibody specificity exchanger of the invention can be used as a diagnostic reagent instead of antisera or monoclonal antibodies in testing systems, and in vivo it can be used to redirect antigens or antibodies to other antibodies or antigens, respectively, than they were originally directed to.

BACKGROUND

During the past decade the antigenic structure of several viral proteins have been characterized using synthetic peptides, such as the human immunodeficiency virus-1 (HIV-1)gp160, and the hepatitis B virus core/e antigens (HBc/eAg). Recently it has been shown that a synthetic peptide corresponding to the complementarity determining region 3 of the heavy chain (CDRH3) of a monoclonal antibody (mAb; F58), directed to the variable third (V3) domain of HIV-1 gp160, may act as a mini antibody and neutralize HIV-1 in vitro. In the experimental part of the present specification, the construction of synthetic peptides combining the CDRH3 domain of the mAb F58, or CDRH1, CDRH2, CDRH3 domain of Ab C1–5, and antigenic regions derived from the HIV-1 gp41, HBc/e antigen, hepatitis C virus (HCV) core protein or from the poliovirus VP1, is shown. These peptides specifically bound the V3 domain of HIV-1. Thus, it was possible to modify the antigenic surface of HIV-1 V3 peptides. This antigen/antibody specificity exchanger will be used for redirecting the reactivity of circulating antibodies and using already existing antibody specificities for a predetermined purpose. It may also serve to alter the composition of the surface of proteins by the addition of foreign determinants. For example, the widely used poliovirus vaccination, together with the high rate of seropositivity to enteroviral proteins may be a suitable pool of antibodies to redirect against other pathogens, such as HIV.

The complementary determining regions (CDRs) of antibodies are responsible for the specificity of the antibody (1,2). X-ray crystallography has shown that the three CDRs of the variable (V) region of the heavy chain and the three CDRs of the V region of the light chain may all have contact with the epitope in an antigen-antibody complex (3). Single peptides corresponding to the CDRs of mAbs to various antigens have been shown to mimic the recognition capabilities of the respective mAb (4–10). Recently it was shown that a peptide corresponding to CDRH3 of a mAb specific for the V3 region of human immuno deficiency virus-1, holds neutralizing capacity when assayed in vitro (9). It was also observed that the CDRH2 of a mAb to hepatitis B core antigen (HBcAg) is capable of capturing HBcAg (10).

DESCRIPTION OF THE INVENTION

The present invention is, in one aspect, directed to an antigen/antibody specificity exchanger, which comprises A) an amino-acid sequence corresponding to an amino-acid sequence of an antibody which specifically binds to a certain antigen, including hapten, B) linked by a link to C) an amino-acid sequence to which a certain antibody binds.

The amino-acid sequence of A) may comprise additional amino acids or sequences on one or both sides of the amino-acid sequence of an antibody which specifically binds to a certain antigen, including hapten. Such additional amino acids and sequences may be, but are not limited to, the amino acids and sequences naturally occurring in said antibody as extensions to the amino-acid sequence of A). The number of amino-acid residues in the amino-acid sequence of A) is preferably at least 5, and is together with possible extensions preferably less than 35.

Further, the amino-acid sequence of C) may comprise additional amino acids or sequences on one or both sides of the amino-acid sequence to which a certain antibody binds. Such additional amino acids and sequences may be, but are not limited to, the amino acids and sequences naturally occurring as extensions to the amino-acid sequence of C). The number of amino-acid residues in the amino-acid sequence of C) is preferably at least 5, and is together with possible extensions preferably less than 35.

In an embodiment of the above aspect of the invention said antigen/antibody specificity exchanger of the invention is one wherein said amino-acid sequence of A) corresponds to an amino-acid sequence of a complementarity determining region (CDR) or a framework region of a certain antibody.

In a further embodiment said antigen/antibody specificity exchanger of the invention is one wherein said amino-acid sequence of C) corresponds to an antibody-binding region of a certain protein, such as one of viral, bacterial or fungal origin.

In another embodiment said antigen/antibody specificity exchanger of the invention is one wherein said amino-acid sequence of A) is linked to said amino-acid sequence of C) by a link B), which is selected from the group consisting of a direct peptide bond and spacer molecules, such as an amino acid, an amino acid having two amino groups, linear or branched peptides or polypeptides and biotin-avidin-biotin.

In a preferred embodiment said antigen/antibody specificity exchanger of the invention is one wherein said amino-acid sequence of A) is selected from the group consisting of

SEQ ID NO: 1:

Cys Asp Leu Ile Tyr Tyr Asp Tyr Glu Glu Asp Tyr Tyr Phe

SEQ ID NO: 2:

Cys Asp Leu Ile Tyr Tyr Asp Tyr Glu Glu Asp Tyr Tyr

SEQ ID NO: 3

Thr Tyr Ala Met Asn

SEQ ID NO: 4

Arg Val Arg Ser Lys Ser Phe Asn Tyr Ala Thr Tyr Tyr Ala Asp Ser Val Lys Gly and

SEQ ID NO: 5

Pro Ala Gln Gly Ile Tyr Phe Asp Tyr Gly Gly Phe Ala Tyr

In another preferred embodiment said antigen/antibody specificity exchanger of the invention is one wherein said amino-acid sequence of C) is selected form the group consisting of

SEQ ID NO: 6:

Pro Pro Asn Ala Pro Ile Leu Ser

SEQ ID NO: 7:

Arg Pro Pro Asn Ala Pro Ile Leu Ser Thr

SEQ ID NO: 8:

Lys Glu Ile Pro Ala Leu Thr Ala Val Glu Thr Gly

SEQ ID NO: 9:

Pro Ala His Ser Lys Glu Ile Pro Ala Leu Thr Ala

SEQ ID NO: 10:
Trp Gly Cys Ser Gly Lys Leu Ile Cys Thr
SEQ ID NO: 11:
Cys Thr Thr Ala Val Pro Trp Asn Ala Ser and
SEQ ID NO: 12:
Gln Arg Lys Thr Lys Arg Asn Thr Asn Arg Arg.

Specific examples of antigen/antibody specificity exchangers of the invention:

Peptide 1:
SEQ ID NO: 13
Cys Asp Leu Ile Tyr Tyr Asp Tyr Glu Glu Asp Tyr Tyr Phe Pro Pro Asn Ala Pro Ile Leu Ser Peptide 2:
SEQ ID NO: 14
Cys Asp Leu Ile Tyr Tyr Asp Tyr Glu Glu Asp Tyr Tyr Phe Arg Pro Pro Asn Ala Pro Ile Leu Ser Thr Peptide 3:
SEQ ID NO: 15
Cys Asp Leu Ile Tyr Tyr Asp Tyr Glu Glu Asp Tyr Tyr Phe Lys Glu Ile Pro Ala Leu Thr Ala Val Glu Thr Gly Peptide 4:
SEQ ID NO: 16
Cys Asp Leu Ile Tyr Tyr Asp Tyr Glu Glu Asp Tyr Tyr Phe Pro Ala His Ser Lys Glu Ile Pro Ala Leu Thr Ala Peptide 5:
SEQ ID NO: 17
Cys Asp Leu Ile Tyr Tyr Asp Tyr Glu Glu Asp Tyr Tyr Phe Trp Gly Cys Ser Gly Lys Leu Ile Cys Thr Peptide 6:
SEQ ID NO: 18
Cys Asp, Leu Ile Tyr Tyr Asp Tyr Glu Glu Asp Tyr Tyr Phe Cys Thr Thr Ala Val Pro Trp Asn Ala Ser Peptide 7:
SEQ ID NO: 19
Cys Asp Leu Ile Tyr Tyr Asp Tyr Glu Glu Asp Phe Lys Arg Pro Pro Asn Ala Pro Ile Leu Ser Thr Cys Asp Leu Ile Tyr Tyr Asp Tyr Glu Glu Asp Tyr Phe Peptide 8:
SEQ ID NO: 20
Thr Tyr Ala Met Asn Pro Pro Asn Ala Pro Ile Leu Ser Peptide 9:
SEQ ID NO: 21
Arg Val Arg Ser Lys Ser Phe Asn Tyr Ala Thr Tyr Tyr Ala Asp Ser Val Lys Gly Pro Pro Asn Ala Pro Ile Leu Ser Peptide 10:
SEQ ID NO: 22
Pro Ala Gln Gly Ile Tyr Phe Asp Tyr Gly Gly Phe Ala Tyr Pro Pro Asn Ala Pro Ile Leu Ser Peptide 11:
SEQ ID NO: 23
Cys Asp Leu Ile Tyr Tyr Asp Tyr Glu Glu Asp Tyr Tyr Gln Arg Lys Thr Lys Arg Asn Thr Asn Arg Arg Another aspect of the invention is directed to a diagnostic reagent comprising an antigen/antibody specificity exchanger according to the invention.

Such a diagnostic reagent of the invention may be used to detect in vitro specific antigens in-biological samples, e.g. body fluid or tissue samples. Thus, the diagnostic reagent of the invention may be used instead of antisera or monoclonal antibodies in in vitro testing systems, such as immunological tests, e.g. Enzyme-Linked Immunosorbent Assay (ELISA), Enzyme Immunoassay (EIA), Western Blot, Radioimmunoassay (RIA) etc. Further, the diagnostic reagent of the invention may be used to investigate biological properties of biological systems.

Still another aspect of the invention is directed to a method of treating a disease or disorder caused by a known antigen in an individual in need of an increased number of antigen-specific antibodies, which comprises administration to said individual of a sufficient amount of a tailor-made antigen/antibody specificity exchanger according to the invention which binds to certain antibodies known to exist in said individual.

An individual in need of an increased number of antigen-specific antibodies against a known antigen, which causes a disease or disorder in said individual, may be one who will benefit from getting a rapid increase in the number of such antigen-specific antibodies, or who even lacks or has insufficient ability to elicit antibodies against said known antigen. Said individual may be a human or non-human mammal.

Such a tailor-made antigen/antibody specificity exhanger according to the invention is designed so that certain antibodies existing in the patient in question, (e.g. antibodies against viral proteins, such as antibodies against poliovirus, antibodies against virus causing measles, antibodies against hepatitis B virus, antibodies against hepatitis C virus, antibodies against HIV-1, whether induced by natural infection or vaccination) binds to the amino-acid sequence of C) and the amino-acid sequence of A) binds to a known antigen causing a disease or disorder in said patient (e.g. HIV).

Thus, existing antibodies in said patent are redirected to said known antigen (against which said patient e.g. lacks or has insufficient amount of desired antibodies).

A specific example of an antigen/antibody specificity exchanger of the invention is a peptide which binds to antibodies against poliovirus and also binds specifically to HIV virus. Thus, already high titres in a patient of antibodies against poliovirus may thus be used to fight HIV infection in said patient.

Preparation of the Antigen/Antibody Specificity Exchanger of the Invention

The antigen/antibody specificity exchanger of the invention is prepared in any suitable manner known in the art. It is in most cases a peptide, with the exception of the case when it comprises biotin-avidin-biotin as a linker. As is well-know in the art, peptides can be produced by genetic engineering methods or peptide synthesis. In peptide synthesis one amino-acid residue is coupled to the next one in liquid phase, or starting with the solid phase to which the C-terminal of the first amino acid is coupled, whereupon the C-terminal of the next amino acid is coupled to the N-terminal of the first amino acid, etc, finally releasing the build-up peptide from the solid phase.

The antigen/antibody specificity exchangers presented in Table 1 are all synthetic peptides synthesized according to a method for multiple peptide synthesis (21) and by a Milligen 9050 peptide synthesizer using 9-fluorenylmethoxy-carbonyl-protected amino acid esters (20). All peptides were analysed and/or purified by reverse phase HPLC using a Pep-S 5 m column (Pharmacia-LKB, Uppsala, Sweden), run with a gradient from 10% to 60% CH3CN against water containing 0.1% trifluoro-acetic acid.

Testing of the Antigen/Antibody Specificity Exchanger of the Invention

Monoclonal antibodies and human sera. The production and characterization of mAb to HBc/eAg has been described (15, 18). The mAb 14E11 recognizes the epitope at residues 135–141 (PNAPILS), of the HBc/eAg sequence (15). The monoclonal antibody 14E11 was kindly provided by Dr. Alexander Cimanis, Riga. Two human sera (A and B) reactive to a peptide covering residues 42–55 of VP1 of poliovirus 1 have previously been described (19). A monoclonal antibody against enteroviral VP1 was purchased from Dako (CBV; M7064, Dako, Copenhagen, Denmark).

Three human sera (C, D and E) positive for antibodies to hepatitis C virus (HCV) core residues 7–19 have previously been described (20).

Enzyme immuno assays (EIAs). Strain-specific HIV-1 V3 peptides were coated on microtiter wells (Nunc 96F Certificated; Nunc, Copenhagen, Denmark) in 100 ml portions at concentrations of from 10 mg/ml to 0.01 mg/ml in 0.05 M sodium carbonate buffer, pH 9.6, at +4° C. overnight. Excess peptides were removed by washing with PBS containing 0.05% Tween 20. The peptide-coated plates were assayed for binding using the peptides of the invention diluted from 100 mg/ml to 0.01 mg/ml in PBS containing 1% BSA, 2% goat serum, and 0.05% Tween 20. The dilutions of the peptides of the invention were added in 100 ml portions and incubated with the adsorbed V3 peptides for 60 minutes at +37° C. Excess test peptides were removed by washing and bound peptide was indicated by the respective mAb or anti-serum, by incubation for 60 minutes at +37° C. The amount of bound antibody was indicated by an additional incubation of enzyme-labelled secondary antibody, rabbit anti-mouse Ig (P260, Dako, Copenhagen, Denmark) for mAbs, and goat anti-human IgG (A-3150; Sigma Chemicals, St. Louis, Mo.) for human antibodies. The amount of bound conjugate was determined by addition of substrate and the absorbances were measured at 492 nm or 405 nm in a spectrophoto-meter.

Antibody recognition of peptides of the invention. When adsorbed to microplates all peptides of the invention presented in Table 1 except for Nos. 4 (Table 2) and 7 (data not shown) were found to be reactive with the respective antibodies.

Antigen binding of the peptides of the invention. The anti-genically functional test peptides were further evaluated for binding of HIV-1 V3 peptide, MN-strain. All test peptides which had a functional antigenic region were found to directly bind to the HIV-1 V3 peptide (Tables 3 and 4). As shown in Tables 3 and 4, the reactivity to the HIV-1 V3 peptide was found to be dependent on both concentrations of the test peptides and of V3 peptides, indicating a specific reactivity. This clearly indicates that it was possible to redirect antibodies specific for HIV-1 gp41, HBc/eAg and poliovirus 1 VP1 to bind to the altered antigenic surface of the HIV-1 V3 peptide. It was also found, that pre-incubation of equimolar concentrations of mAb 14E11 and the corresponding test peptide of the invention, did not change the ability of the test peptide mAb complex to bind to the V3 peptide (data not shown). This indicates that it is possible to add antigenic domains to a CDR peptide with retained antigen binding ability of the CDR sequence.

The ability of the antigen/antibody specificity exchangers to redirect antibodies was further evaluated in a system where the CDRH1, CDRH2 and CDRH3 sequences from mAb C1–5 were added to the epitope sequence for mAb 14E11. A peptide corresponding to the epitope sequence for mAb C1–5, residues 71–90 of HBc/eAg with an Ile at position 80, was adsorbed to microplates. The antigen/antibody specificity exchangers, based on the C1–5 CDRs, were then added, and the amount bound CDR peptide was indicated by the epitope specific mAb 14E11. The results clearly showed that the mAb 14E11 which originally recognized residues 134–141 of the HBc/eAg sequence was redirected by the antigen/antibody specificity exhanger containing the CDRH2 sequence (Table 5). Also, this reactivity was dependent on the amount CDR added, indicating a specific reaction ($p<0.01$, Regression analysis; Table 5).

Further, in Table 7 is shown that the antigen/antibody specificity exchanger of the invention can redirect an existing HBc/eAg specific antibody to significantly bind to HIV-1 V3 peptides of several different subtypes.

Thus, it is evident that the antigen/antibody exchanger of the invention forms the basis of a novel method for redirecting the specificity of monoclonal and polyclonal antibodies by modifying the antigenic surface of a viral protein.

It should be understood that the invention comprises antigen/antibody exchangers wherein included amino-acid sequences are chemically stabilized e.g. by cyclization and wherein included amino-acid sequences may have specific amino-acid deletions, additions and/or substitutions. Such modified amino-acid sequences may result in antigen/antibody exchangers exhibiting increased (or decreased) biological activities.

TABLE 1

Antigen/antibody specificity exchangers of the invention represented by peptides containing the CDRH3 domain of mAb F58 or CDRH1, CDRH2, CDRH3 domain of mAb C1–5 (A) and different antigenic regions derived from viral proteins (C)

| Peptide No. | Amino-acid sequence (A) | link (B) | Amino-acid sequence (C) | Source of aas (C) | Ref. |
|---|---|---|---|---|---|
| 1. | SEQ ID NO 1. | peptide bond | SEQ ID NO 6 | HBc/eAg, aas 134–141 | 15 |
| 2. | SEQ ID NO 1. | peptide bond | SEQ ID NO 7 | HBc/eAg, aas 133–142 | 15 |
| 3. | SEQ ID NO 1. | peptide bond | SEQ ID NO 8 | Polio VP1, aas 39–50 | 16 |
| 4. | SEQ ID NO 1. | peptide bond | SEQ ID NO 9 | Polio VP1, aas 35–46 | 16 |
| 5. | SEQ ID NO 1. | peptide bond | SEQ ID NO 10 | HIV-1 gp41, aas 596–605 | 20 |
| 6. | SEQ ID NO 1. | peptide bond | SEQ ID NO 11 | HIV-1 gp41 aas 603–612 | 20 |
| 7. | 2(SEQ ID NO 1) | Lys | SEQ ID NO 7 | HBc/eAg, aas 133–142 | 15 |
| 8. | SEQ ID NO 3. | peptide bond | SEQ ID NO 6 | HBc/eAg, aas 134–141 | 15 |
| 9. | SEQ ID NO 4. | peptide bond | SEQ ID NO 6 | HBc/eAg, aas 134–141 | 15 |

TABLE 1-continued

Antigen/antibody specificity exchangers of the invention represented by peptides containing the CDRH3 domain of mAb F58 or CDRH1, CDRH2, CDRH3 domain of mAb C1–5 (A) and different antigenic regions derived from viral proteins (C)

| Peptide No. | Amino-acid sequence (A) | link (B) | Amino-acid sequence (C) | Source of aas (C) | Ref. |
|---|---|---|---|---|---|
| 10. | SEQ ID NO 5. | peptide bond | SEQ ID NO 6 | HBc/eAg, aas 134–141 | 15 |
| 11. | SEQ ID NO 2. | peptide bond | SEQ ID NO 12 | HCV core 8–18 | 22 |

Note: aas=amino acids

TABLE 2

Testing of antigen/antibody specificity exchanger of the invention represented by peptides passively adsorbed to polystyrene for ability to be recognized by antibodies specific for the antigenic region presented in the peptide. Values are given as the absorbance obtained at 492 or 405 nm

| Peptide | Antibody | Amount peptide added (ng/0.1 ml) to solid phase | | | | | |
|---|---|---|---|---|---|---|---|
| No. | used | 1.000 | 100 | 10 | 1 | 0.1 | 0.01 |
| 1 | 14E11 | 2.500 | 1.675 | 0.030 | 0.010 | 0.009 | 0.008 |
| 2 | 14E11 | 2.500 | 1.790 | 0.008 | 0.006 | 0.008 | 0.006 |
| 3 | CBV | 2.500 | 1.142 | 0.036 | 0.020 | 0.019 | 0.036 |
| | human A | 1.945 | 1.850 | 0.486 | 0.088 | 0.115 | 0.116 |
| | human B | 1.342 | 0.770 | 0.130 | 0.065 | 0.090 | 0.095 |
| 4 | CBV | 0.020 | 0.018 | 0.015 | 0.016 | 0.017 | 0.018 |
| | human A | 0.059 | 0.081 | 0.108 | 0.109 | 0.097 | 0.100 |
| | human B | 0.052 | 0.072 | 0.091 | 0.098 | 0.083 | 0.100 |

Note: Regression analysis of the relation between absorbance and peptide concentration gives $p<0.01$.

TABLE 3

Testing of the HIV-1 V3 peptide-antigen binding capability of the CDR sequence simultaneously with the ability to be recognized by monoclonal antibodies specific for the antigenic region on the test peptide of the invention. Values are given as the absorbance at 492 nm a:

| Peptide | Antibody | Amount of test peptide | Amount V3 peptide added (ng/0.1 ml) to solid phase | | | | | |
|---|---|---|---|---|---|---|---|---|
| No. | used | (ng/0.1 ml) | 1.000 | 500 | 250 | 125 | 62.5 | 31.25 |
| 1 | 14E11 | 10,000 | 2.500 | 2.500 | 2.500 | 2.338 | 1.702 | 1.198 |
| | | 5,000 | 2.500 | 2.500 | 2.500 | 2.190 | 1.622 | 1.122 |
| | | 2,500 | 2.500 | 2.500 | 2.500 | 2.039 | 1.394 | 0.990 |
| | | 1,250 | 2.500 | 2.500 | 2.500 | 1.712 | 0.930 | 0.771 |
| | | 625 | 1.936 | 0.824 | 0.380 | 0.152 | 0.056 | 0.053 |
| | | 312 | 0.196 | 0.085 | 0.044 | 0.043 | 0.030 | 0.025 |

b:

| Peptide | Antibody | Amount of test peptide | Amount of V3 peptide added (ng/0.1 ml) | | | | | |
|---|---|---|---|---|---|---|---|---|
| No. | used | (ng/0.1 ml) | 1.000 | 500 | 250 | 125 | 62.5 | 31.25 |
| 4 | 14E11 | 10.000 | 2.500 | 2.500 | 2.133 | 1.560 | 1.070 | 0.829 |
| | | 5.000 | 2.500 | 2.500 | 1.963 | 1.645 | 1.074 | 0.981 |
| | | 2.500 | 2.500 | 2.500 | 1.729 | 1.404 | 0.962 | 0.747 |
| | | 1.250 | 2.500 | 2.424 | 1.433 | 1.327 | 0.795 | 0.488 |

TABLE 3-continued

Testing of the HIV-1 V3 peptide-antigen binding capability of the CDR sequence simultaneously with the ability to be recognized by monoclonal antibodies specific for the antigenic region on the test peptide of the invention. Values are given as the absorbance at 492 nm

| | | | | | | | | |
|---|---|---|---|---|---|---|---|---|
| | | 625 | 0.835 | 0.359 | 0.200 | 0.120 | 0.088 | 0.073 |
| | | 312 | 0.099 | 0.054 | 0.042 | 0.049 | 0.045 | 0.025 |

c:

| Peptide | Antibody | Amount of test peptide | Amount peptide added (ng/0.1 ml) to solid phase | | | | | |
|---|---|---|---|---|---|---|---|---|
| No. | used | (ng/0.1 ml) | 1.000 | 100 | 10 | 1 | 0.1 | 0.01 |
| 3 | CBV | 10,000 | 0.523 | 0.498 | 0.162 | 0.161 | 0.017 | 0.017 |
| | | 1,000 | 0.053 | 0.054 | 0.031 | 0.027 | 0.010 | 0.010 |
| | | 100 | 0.034 | 0.037 | 0.025 | 0.029 | 0.010 | 0.010 |
| | | 10 | 0.023 | 0.022 | 0.014 | 0.014 | 0.010 | 0.009 |
| | | 1 | 0.013 | 0.044 | 0.014 | 0.017 | 0.027 | 0.009 |
| | | 0.1 | 0.011 | 0.009 | 0.008 | 0.032 | 0.013 | 0.013 |

Note: Regression analysis of the relation between absorbance and CDR peptide concentration, and relation between absorbance and V3 peptide concentration gives $p<0.01$, respectively.

TABLE 4

Testing of the HIV-1 V3 peptide antigen binding capability of the CDR sequence simultaneously with the ability to be recognized by human anti-polio VP1 polyclonal antibodies specific for the antigenic region on the test peptides of the invention. Values are given as the absorbance at 405 nm

| Peptide | Antibody | Amount of test peptide | Amount V3 peptide added (ng/0.1 ml) to solid phase | | | | | |
|---|---|---|---|---|---|---|---|---|
| No. | used | (ng/0.1 ml) | 1.000 | 500 | 250 | 125 | 62.5 | 31.25 |
| a: | | | | | | | | |
| 3 | human A | 10,000 | 1.538 | 1.356 | 1.448 | 1.052 | 0.280 | 0.123 |
| | | 5,000 | 1.179 | 1.050 | 1.006 | 0.557 | 0.136 | 0.087 |
| | | 2,500 | 0.684 | 0.558 | 0.604 | 0.216 | 0.084 | 0.067 |
| | | 1,250 | 0.367 | 0.358 | 0.332 | 0.162 | 0.075 | 0.062 |
| | | 625 | 0.228 | 0.238 | 0.220 | 0.121 | 0.083 | 0.063 |
| | | 312 | 0.171 | 0.154 | 0.154 | 0.103 | 0.072 | 0.060 |
| b: | | | | | | | | |
| 3 | human B | 10,000 | 0.366 | 0.352 | 0.352 | 0.200 | 0.074 | 0.056 |
| | | 5,000 | 0.206 | 0.217 | 0.188 | 0.131 | 0.063 | 0.053 |
| | | 2,500 | 0.134 | 0.132 | 0.126 | 0.091 | 0.061 | 0.055 |
| | | 1,250 | 0.107 | 0.114 | 0.108 | 0.077 | 0.060 | 0.054 |
| | | 625 | 0.082 | 0.104 | 0.087 | 0.075 | 0.063 | 0.056 |

TABLE 4-continued

Testing of the HIV-1 V3 peptide antigen binding capability of the CDR sequence simultaneously with the ability to be recognized by human anti-polio VP1 polyclonal antibodies specific for the antigenic region on the test peptides of the invention. Values are given as the absorbance at 405 nm

| Peptide No. | Antibody used | Amount of test peptide (ng/0.1 ml) | Amount V3 peptide added (ng/0.1 ml) to solid phase 1.000 | 500 | 250 | 125 | 62.5 | 31.25 |
|---|---|---|---|---|---|---|---|---|
| | | 312 | 0.083 | 0.091 | 0.094 | 0.077 | 0.068 | 0.060 |

Note: Regression analysis of the relation between absorbance and CDR peptide concentration, and relation between absorbance and V3 peptide concentration gives $p<0.01$, respectively.

TABLE 5

Testing of the HIV-1 V3 peptide antigen capability of the CDR sequence simultaneous with the ability to be recognized by human anti-HCV core polyclonal antibodies specific for the antigenic region on the test peptides of the invention. Values are given as the absorbance at 405 nm

| Peptide No. | Antibody used | Amount of V3 peptide (ng/0.1 ml) | Amount of test peptide added (ng/0.1 ml) 62 | 31 | 15 | 7.5 | 3.7 | 1.8 |
|---|---|---|---|---|---|---|---|---|
| 11 | human | 625 | 2.500 | 2.416 | 2.097 | 1.473 | 0.973 | 0.630 |
| | HCV-C | 78 | 2.500 | 2.335 | 1.781 | 1.225 | 0.825 | 0.564 |
| | | 39 | 2.389 | 2.287 | 1.626 | 1.081 | 0.664 | 0.389 |
| 11 | human | 625 | 1.999 | 1.490 | 1.184 | 0.751 | 0.458 | 0.428 |
| | HCV-D | 78 | 1.758 | 1.370 | 1.025 | 0.612 | 0.468 | 0.380 |
| | | 39 | 1.643 | 0.993 | 0.833 | 0.497 | 0.343 | 0.287 |
| 11 | human | 625 | 2.368 | 2.165 | 1.656 | 1.104 | 0.645 | 0.462 |
| | HCV-E | 78 | 2.156 | 1.824 | 1.396 | 0.733 | 0.514 | 0.352 |
| | | 39 | 1.893 | 1.683 | 1.110 | 0.756 | 0.310 | 0.272 |

TABLE 7

Redirecting existing HBc/eAg specific antibody (14E11, from Dr. A. Tsimanis, Riga) to different subtype-specific HIV-1 V3 peptides (subtypes A–E) via specificity exchanger peptide containing CDRH3 sequence against HIV-1 and a HBc/eAg epitope for mAb 14E11

| HIV-1 V3 peptide attached to solid-phase | Reactivity (absorbance at 405 nm) of specificity exchanger peptide added in the indicated amount (ng) 500 | 250 | 125 | 62.5 | 31.25 | 15.625 |
|---|---|---|---|---|---|---|
| Subtype A | 0.378 | 0.126 | 0.078 | 0.068 | 0.062 | 0.017 |
| Subtype B | 2.686 | 2.536 | 1.710 | 1.329 | 0.360 | 0.157 |
| Subtype C | 1.261 | 0.514 | 0.111 | 0.077 | 0.051 | 0.020 |
| Subtype D | 0.17 | 0.079 | 0.065 | 0.028 | 0.029 | 0.026 |
| Subtype E | 0.22 | 0.090 | 0.093 | 0.032 | 0.063 | 0.030 |

References

1. Kabat, E. A., Wu, T. T. & Bilofsky, H. (1976) Proc Natl Acad Sci USA 73, 4471.
2. Kieber, E. T. & Kohler, H. (1986) Immunol Rev 90, 29.
3. Amit, A. G., Maruzzia, R. A., Phillips, S. E. V. & Poljak, R. J. (1986) Science 233, 747.
4. Williams, W. V., Guy, R., Rubin, D. H., Robey, F., Myers, J. N., Kieber, E. T., Weiner, D. B. & Greene, M. I. (1988) Proc Natl Acad Sci USA 85, 6488.
5. Williams, W. V., Moss, D. A., Kieber, E. T., Choen, J. A., Myers, J. N., Weiner, D. B. & Green, M. L. (1989) Proc. Natl. Acad. Sci. USA 87, 5537.
6. Taub, R., Gould, R. J., Garsky, V. M., Ciccarone, T. M., Hoxie, J., Friedman, P. A. & Shattil, S. J. (1989) J. Biol. Chem. 264, 259.
7. Cohen, J. A., Williams, W. W., Weiner, D. B., Geller, H. M. & Greene, M. I. (1990) Proc. Natl. Acad. Sci. USA 87, 492.
8. Williams, V. W., Kieber, E. T., VonFeldt, J., Greene, M. I. & Weiner, D. B. (1991) J. Biol. Chem. 266, 5182.
9. Levi, M., Sällberg, M., Rudén, U., Herlyn, D., Maruyarna, H., Wigzell, H., Marks, J. & Wahren, B. (1993) Proc Natl Acad Sci USA 90, 4374.

TABLE 6

Testing of C1–5 CDRs (10 ug/ml) (in test peptides of the invention) with a peptide corresponding to HBc/eAg corresponding to residues 71–90) coated on solid phase. Bound CDR was indicated by the epitope specific mAb 14E11

| CDR sequence | Antibody used | Amount c71–90 peptide (ng/0.1 ml) | Amount of test peptide added (ng/0.1 ml) 10.000 | 5.000 | 2.500 | 1.250 | 625 | 312 |
|---|---|---|---|---|---|---|---|---|
| Peptide 8: | 14E11 | 625 | 0.003 | 0.002 | 0.002 | 0.002 | 0.002 | 0.002 |
| CDRH1 | | 312 | 0.002 | 0.002 | 0.004 | 0.003 | 0.006 | 0.004 |
| (SEQ ID NO 3) | | 78 | 0.003 | 0.003 | 0.005 | 0.005 | 0.003 | 0.003 |
| Peptide 9: | 14E11 | 625 | 2.500 | 1.303 | 0.070 | 0.012 | 0.003 | 0.002 |
| CDRH2 | | 312 | 2.500 | 1.070 | 0.058 | 0.011 | 0.003 | 0.002 |
| (SEQ ID NO 4) | | 78 | 2.500 | 0.868 | 0.039 | 0.008 | 0.003 | 0.003 |
| Peptide 10: | 14E11 | 625 | 0.004 | 0.003 | 0.004 | 0.003 | 0.003 | 0.003 |
| CDRH3 | | 312 | 0.004 | 0.003 | 0.004 | 0.004 | 0.003 | 0.003 |
| (SEQ ID NO 5) | | 78 | 0.005 | 0.004 | 0.005 | 0.005 | 0.004 | 0.004 |

10. Sällberg. M., Levi, M., Rudén, U., Pushko, P., Bichko, V., Magnius, L. O., Tsimanis, A. & Wahren, B. in Peptides: Chemistry and Biology (eds. Hodges, R. & Rivier, J.) In press (ESCOM, Leiden, 1993).
11. Machida, A., Ohnuma, H., Takai, E., Tsuda, F., Tanaka, T., Naito, M., Munekata, E., Miyakawa, Y. / Mayurni, m. (1989) Mol. Immunol. 26, 431.
12. Salfeld, J., Pfaff, E., Noah, M. & Schaller, H. (1989) J. Virol. 63, 798.
13. Sällberg, M., Rudén, U., Magnius, L.O., Harthus, H. P., Noah, M. & Wahren, B. (1991) J. Med. Virol. 33, 248.
15. Sällberg, M., Pushko, P., Berzinsh, I., Bishko, V., Sillekens, P., Noah, M., Pumpens, P., Gren, E., Wahren, B. & Magnius, L. O. (1993) J. Gen. Virol. 74, 1335.
16. Roivanen, M., Närvänen, A., Korkolainen, M., Huhtala, M-L & Hovi, T. (1991) Virol 180, 99–107.
18. Bichko, V. V., Schodel, F., Nassal, M., Grene, E., Berzinsh, I., Borisova, G., Miska, S., Peterson, D. L, Gren, E. & Will, H. (1993) Mol. Immunol. 30, 221.
19. Cello, J., Samuelsson, A., Stålhandske, P., Svennerholm, B., Jeansson, S. & Forsgren, M. (1993) J. Clin. Microbiol. 31, 911–916.
20. ZX Zhang, M Chen, K Wallhagen, J Trojnar, L O Magnius, B Wahren, & M Sallberg. Molecular basis for antibody cross-reactivity between the hepatitis C virus core protein and the host-derived GOR protein. Clin. Exp. Immunol. 1994; in press.
21. Hougthen, R. A. (1985) Proc. Natl. Acad. Sci. USA 82, 5131.

---

What is claimed is:

1. An antigen/antibody specificity exchanger comprising a first specific binding sequence that specifically binds to a hepatitis viral antigen covalently linked to a second sequence comprising an epitope of a pathogen.

2. The antigen/antibody exchanger of claim 1, wherein the hepatitis viral antigen is a hepatitis core antigen or a hepatitis e antigen.

3. The antigen/antibody exchanger of claim 2, wherein the pathogen is a herpes simplex virus.

* * * * *